United States Patent [19]
Hillman et al.

[11] Patent Number: 5,889,170
[45] Date of Patent: Mar. 30, 1999

[54] HUMAN INTEGRAL MEMBRANE PROTEIN

[75] Inventors: Jennifer L. Hillman, San Jose; Surya K. Goli, Sunnyvale, both of Calif.

[73] Assignee: Incyte Pharmaceuticals, Inc., Palo Alto, Calif.

[21] Appl. No.: 791,338

[22] Filed: Jan. 31, 1997

[51] Int. Cl.$^6$ .......................... C07H 21/04; C12N 15/63; C12N 1/21
[52] U.S. Cl. .................... 536/23.5; 435/69.1; 435/252.3; 435/320.1
[58] Field of Search ................................ 536/23.1, 23.5; 935/9; 435/69.1, 252.3, 320.1

[56] References Cited

FOREIGN PATENT DOCUMENTS

9316178 A  8/1993  WIPO .
9514772    1/1995  WIPO .

OTHER PUBLICATIONS

Lazar et al. Mol. Cell. Biol. 8 : 1247–1252, 1988.
Tao et al. J. Immunol. 143 (8) : 2595–2601, 1989.
Gillies, et al. Human Antibod & Hybridomas 1(1):47–54, 1990.
Hillier,L. et al. GenBank, Accession Nos. AA 149631 and N51010, 1995.
Burgess et al. J. Cell Biol 11: 2129–2138, 1990.
Database EMBL, entry HS690212, Accession No. H62690, Oct. 11, 1995.
Database EMBL, entry HS393355, Accession No. W67393, Jun. 16, 1996.
Database EMBL, entry HSHG2998, Accession No. D45302, Dec. 29, 1995.
Singer, S.J. et al., "The structure and insertion of integral proteins in membranes", *Annu. Rev. Cell Bio.*, 6: 247–296 (1990).
Deleersnijder, W. et al., "Isolation of markers for chondro–osteogenic differentiation using cDNA library subtraction", *J. Biol. Chem.*, 271: 19475–19482 (1996).

*Primary Examiner*—Toni R. Scheiner
*Assistant Examiner*—Nancy A. Johnson
*Attorney, Agent, or Firm*—Lucy J. Billings; Incyte Pharmaceuticals, Inc.

[57] ABSTRACT

The present invention provides a novel human integral membrane (IMP-2) and polynucleotides which identify and encode IMP-2. The invention also provides genetically engineered expression vectors and host cells comprising the nucleic acid sequences encoding IMP-2 and a method for producing IMP-2. The invention also provides for agonists, antibodies, or antagonists specifically binding IMP-2, and their use, in the prevention and treatment of diseases associated with expression of IMP-2. Additionally, the invention provides for the use of antisense molecules to polynucleotides encoding IMP-2 for the treatment of diseases associated with the expression of IMP-2. The invention also provides diagnostic assays which utilize the polynucleotide, or fragments or the complement thereof, and antibodies specifically binding IMP-2.

8 Claims, 11 Drawing Sheets

```
NNG CCT CTG CCG CGG ACT TCC CGA ACC TCT TCA GCC CGG AGC CGC         54
                18          27          36          45

TCC CGG AGC CCG GCC CCG GCC GTA GAG GCT GCA ATC GCA GCC GGT GAG CCC GCA GCC CGC   108
     63          72          81          90          99

GCC CCG AGC CCG CCC TTC GAG GGC GCC CGC CCA GGC GCC CGC ATG GTG AAG           162
    117         126         135         144         153
                                                  M   V   K

GTG ACG TTC AAC TCC GCT CTG GCC CAG AAG GAG GCC AAG AAG GAG GAC GAG CCC AAG   216
 V   T   F   N   S   A   L   A   Q   K   E   A   K   K   E   D   E   P   K
    171         180         189         198         207

AGC GGC GAG GAG GCG CTC ATC ATC CCC CCC GAC GCC GTC GCG GAC TGC AAG           270
 S   G   E   E   A   L   I   I   P   P   D   A   V   A   D   C   K
    225         234         243         252         261

GAC CCA GAT GAT GTG CCA GTT GGC CAA AGA AGA GCC TGG TGT TGG TGC ATG           324
 D   P   D   D   V   P   V   G   Q   R   R   A   W   C   W   C   M
    279         288         297         306         315

TGC TTT GGA CTA GCA TTT ATG CTT GCA GGT GTT ATT CTA GGA GGA TAC TTG           378
 C   F   G   L   A   F   M   L   A   G   V   I   L   G   G   A   Y   L
    333         342         351         360         369
```

FIGURE 1A

```
        387             396             405             414             423             432
TAC AAA TAT TTT GCA CTT CAA CCA GAT GAC GTG TAC TAC TGT GGA ATA AAG TAC
 Y   K   Y   F   A   L   Q   P   D   D   V   Y   Y   C   G   I   K   Y 441             450             459             468             477             486
ATC AAA GAT GAT GTC ATC TTA AAT GAG CCC TCT GCA GAT GCC CCA GCT GCT CTC
 I   K   D   D   V   I   L   N   E   P   S   A   D   A   P   A   A   L 495             504             513             522             531             540
TAC CAG ACA ATT GAA GAA AAT ATT AAA ATC TTT GAA GAA GAA GTT TTT
 Y   Q   T   I   E   E   N   I   K   I   F   E   E   E   V   E   F 549             558             567             576             585             594
ATC AGT GTG CCT GTC CCA GAG TTT GCA GAT AGT GAT CCT GCC AAC ATT GTT CAT
 I   S   V   P   V   P   E   F   A   D   S   D   P   A   N   I   V   H 603             612             621             630             639             648
GAC TTT AAC AAG AAA CTT ACA GCC TAT TTA GAT CTT AAC CTG GAT AAG TGC TAT
 D   F   N   K   K   L   T   A   Y   L   D   L   N   L   D   K   C   Y 657             666             675             684             693             702
GTG ATC CCT CTG AAC ACT TCC ATT GTT ATG CCA CCC AGA AAC CTA CTG GAG TTA
 V   I   P   L   N   T   S   I   V   M   P   P   R   N   L   L   E   L 711             720             729             738             747             756
CTT ATT AAC ATC AAG GCT GGA ACC TAT TTG CCT CAG TCC TAT CTG ATT CAT GAG
 L   I   N   I   K   A   G   T   Y   L   P   Q   S   Y   L   I   H   E
```

FIGURE 1B

```
     765         774         783         792         801         810
CAC ATG GTT ATT ACT GAT CGC ATT GAA AAC ATT GAT CAC CTG GGT TTC TTT ATT
 H   M   V   I   T   D   R   I   E   N   I   D   H   L   G   F   F   I 819         828         837         846         855         864
TAT CGA CTG TGT CAT GAC AAG GAA ACT TAC AAA CTG CAA CGC AGA GAA ACT ATT
 Y   R   L   C   H   D   K   E   T   Y   K   L   Q   R   R   E   T   I 873         882         891         900         909         918
AAA GGT ATT CAG AAA CGT GAA GCC AGC AAT TGT TTC GCA ATT CGG CAT TTT GAA
 K   G   I   Q   K   R   E   A   S   N   C   F   A   I   R   H   F   E 927         936         945         954         963         972
AAC AAA TTT GCC GTG GAA ACT TTA ATT TGT TCT TGA ACA GTC AAG AAA AAC ATT
 N   K   F   A   V   E   T   L   I   C   S   *

981         990         999         1008        1017        1026
ATT GAG GAA AAT TAA TAT CAC AGC ATA ACC CCA CCC TTT ACA TTT TGT GCA GTG 1035        1044        1053        1062        1071        1080
ATT TTT TAA AGT CTT CTT TCA AGT TGT AAG TAG CAA ACA GGG CTT TAC TAT CTT 1089        1098        1107        1116
TTC ATC TCA TTA ATT CAA TTA AAA CCA TTA CCT TAA

FIGURE 1C
```

```
1    MVKVTFNSALAQKEAKKDEPKSGEEAALIIP    632664
1    MVKIAFNTP---TAVQKEEARQDIEALVSR     GI 624778

31   PDAVAVDCKDPDDVVPVGQRRAWCWCMC--     632664
28   TVRAQILTGKELRVVPQEKDGSSGRCMLTL     GI 624778

59   FGLAFMLAGVILGGAYLYKYFALQPDDVYY     632664
58   LGLSFILAGLIVGGACIYKYF-MPKSTIYH     GI 624778

89   CGIKYIKDDVILNEPSADAPAALYQTIEEN     632664
87   GEMCFFDSEDPVNSIPGGEP--YFLPVTEE     GI 624778

119  IKIFEEEVEFISVPVPEFADSDPANIVHD      632664
115  ADIREDDNIAIIDVPVPSFSDSDPAAIIHD     GI 624778

149  FNKKLTAYLDLNLDKCYVIPLNTSIVMPPR     632664
145  FEKGMTAYLDLLLGNCYLMPLNTSIVMTPK     GI 624778

179  NLLELLINIKAGTYLPQSYLIHEHMVITDR     632664
175  NLVELFGKLASGKYLPHTYVVREDLVAVEE     GI 624778
```

| Library | Lib Description | Abun | PctAbun |
|---|---|---|---|
| LIVRNOT01 | liver, 49 M | 841 | 16.6832 |
| LIVRNOM01 | liver, 49 M, WM | 484 | 12.2999 |
| SPLNFET01 | spleen, fetal | 205 | 7.2259 |
| SPLNFEM01 | spleen, fetal, WM | 175 | 5.8024 |
| LIVRFET02 | liver, fetal F | 138 | 3.7923 |
| LIVRBCT01 | liver, primary biliary cirrhosis | 34 | 3.5088 |
| LIVRNOT04 | liver, 32 F, plasmid | 26 | 2.7867 |
| LIVRNOT02 | liver, 32 F | 35 | 1.8097 |
| COCHFEM01 | ear, cochlea, fetal, WM | 6 | 0.6944 |
| NEUTLPT01 | granulocytes, periph blood, M/F, treated LPS | 26 | 0.4505 |
| LVENNOT02 | heart, left ventricle, 39 M | 2 | 0.4193 |
| NEUTGMT01 | granulocytes, M/F periph blood, treated GM-CSF | 20 | 0.3128 |
| PLACNOM01 | placenta, fetal M, WM | 5 | 0.2900 |
| BSTMNON02 | brain stem, 72 M, NORM | 9 | 0.2868 |
| LIVSFEM02 | liver/spleen, fetal M, NORM, WM | 99 | 0.2610 |
| HMC1NOT01 | HMC-1 mast cell line, 52 F | 7 | 0.2341 |
| LATRTUT02 | heart tumor, myoma, 43 M | 17 | 0.2336 |
| NEUTFMT01 | granulocytes, periph blood, M/F, treated fMLP | 13 | 0.2275 |
| LUNGFEM01 | lung, fetal, NORM, WM | 14 | 0.2074 |
| LUNGNOT09 | lung, fetal M | 7 | 0.2001 |
| COLNFET02 | colon, fetal F | 14 | 0.1999 |
| KIDNNOT05 | kidney, neonatal F | 18 | 0.1902 |
| PGANNOT01 | paraganglionic tumor, benign, 46 M | 11 | 0.1759 |
| COLNNOT19 | large intestine, cecum, 18 F | 6 | 0.1756 |
| MENITUT03 | brain tumor, benign meningioma, 35 F | 7 | 0.1745 |
| BRSTNOT01 | breast, 56 F | 9 | 0.1734 |
| LUNGNOT02 | lung, 47 M | 7 | 0.1720 |
| LUNGNOT01 | lung, 72 M | 5 | 0.1690 |
| LUNGNOT12 | lung, 78 M | 6 | 0.1668 |
| CARDFEM01 | heart, fetal, NORM, WM | 20 | 0.1663 |
| LUNGAST01 | lung, asthma, 17 M | 17 | 0.1605 |
| PROSNON01 | prostate, 28 M, NORM | 17 | 0.1600 |
| OVARNON01 | ovary, 59 F, NORM | 1 | 0.1595 |
| ADRENOT07 | adrenal gland, 61 F | 10 | 0.1523 |
| BLADTUT06 | bladder tumor, carcinoma, 58 M | 3 | 0.1521 |
| OVARNOM01 | ovary, 49 F, WM | 2 | 0.1504 |
| EOSIHET02 | eosinophils, hypereosinophilia, 48 M | 14 | 0.1465 |
| RATRNOT02 | heart, right atrium, 39 M | 6 | 0.1423 |
| BRSTTUT02 | breast tumor, 54 F, match to BRSTNOT03 | 10 | 0.1397 |
| BRAINOT10 | brain, cerebellum, Alzheimer's, 74 M | 4 | 0.1393 |
| SCORNON02 | spinal cord, 71 M, NORM | 4 | 0.1381 |
| PANCDIT01 | pancreas, Type I diabetes, 15 M | 3 | 0.1371 |
| BEPINON01 | bronchial epithelium, primary cell line, M | 5 | 0.1368 |
| SYNORAB01 | synovium, hip, rheumatoid, 68 F | 7 | 0.1367 |
| PROSNOT19 | prostate, 59 M | 5 | 0.1358 |
| BRAITUT02 | brain tumor, metastasis, 58 M | 18 | 0.1342 |
| LUNGNOM01 | lung, 72 M, WM | 5 | 0.1336 |
| UTRSNOT02 | uterus, 34 F | 17 | 0.1318 |
| STOMFET01 | stomach, fetal F | 5 | 0.1276 |
| PGANNOT03 | paraganglionic tumor, paraganglioma, 46 M | 4 | 0.1244 |
| COLNNOT07 | colon, 60 M | 3 | 0.1227 |
| COLSUCT01 | colon, sigmoid, ulcerative colitis, 70 M | 3 | 0.1226 |
| PITUNOT02 | pituitary, 15-75 M/F | 9 | 0.1211 |
| LUNGNOT18 | lung, 66 F | 4 | 0.1191 |

FIGURE 4A

| | | | |
|---|---|---|---|
| SYNORAT03 | synovium, wrist, rheumatoid, 56 F | 7 | 0.1187 |
| UTRSNOT01 | uterus, 59 F | 3 | 0.1181 |
| PROSTUT04 | prostate tumor, 57 M, match to PROSNOT06 | 10 | 0.1172 |
| SYNORAT05 | synovium, knee, rheumatoid, 62 F | 4 | 0.1144 |
| LUNGNOT04 | lung, 2 M | 6 | 0.1098 |
| PROSNOT26 | prostate, 65 M | 4 | 0.1080 |
| PTHYTUM01 | parathyroid tumor, adenoma, M/F, NORM, WM | 4 | 0.1071 |
| TLYMNOT01 | lymphocytes (non-adher PBMNC), 24 M | 1 | 0.1070 |
| BRAITUT13 | brain tumor, meningioma, 68 M | 4 | 0.1048 |
| PITUNOT03 | pituitary, 46 M | 3 | 0.1045 |
| PROSNOT07 | prostate, 69 M, match to PROSTUT05 | 3 | 0.1045 |
| COLNNOT11 | colon, 60 M | 7 | 0.1041 |
| SINTFET03 | small intestine, fetal F | 3 | 0.1037 |
| BRSTNOM02 | breast, F, NORM, WM | 5 | 0.1032 |
| LUNGFET03 | lung, fetal F | 15 | 0.1032 |
| PROSNOT14 | prostate, 60 M, match to PROSTUT08 | 4 | 0.1023 |
| BRSTTUT08 | breast tumor, 45 F, match to BRSTNOT09 | 4 | 0.1015 |
| PLACNOB01 | placenta, neonatal F | 4 | 0.1006 |
| OVARNOT03 | ovary, 43 F, match to OVARTUT01 | 6 | 0.1003 |
| THYMNOT02 | thymus, 3 M | 5 | 0.0969 |
| GBLATUT01 | gall bladder tumor, 78 F | 4 | 0.0966 |
| THP1T7T01 | THP-1 promonocyte cell line, untreated | 2 | 0.0965 |
| KIDNNOT02 | kidney, 64 F | 2 | 0.0964 |
| BRSTNOT04 | breast, 62 F | 10 | 0.0960 |
| SYNORAT01 | synovium, elbow, rheumatoid, 51 F | 2 | 0.0956 |
| FIBRNOT01 | WI38 lung fibroblast cell line, 3m F | 2 | 0.0938 |
| OVARTUT01 | ovarian tumor, 43 F, match to OVARNOT03 | 9 | 0.0931 |
| PROSTUT01 | prostate tumor, 50 M, match to PROSNOT02 | 3 | 0.0930 |
| BRAINOT03 | brain, 26 M | 5 | 0.0927 |
| PROSNOT16 | prostate, 68 M | 7 | 0.0921 |
| KERANOT01 | keratinocytes, neonatal M | 4 | 0.0918 |
| THYRNOT02 | thyroid, hyperthyroidism, 16 F | 3 | 0.0910 |
| MPHGNOT03 | macrophages (adher PBMNC), M/F | 7 | 0.0905 |
| OVARNOT02 | ovary, 59 F | 8 | 0.0899 |
| BRAITUT03 | brain tumor, astrocytoma, 17 F | 12 | 0.0890 |
| COLNNOT05 | colon, 40 M, match to COLNCRT01 | 3 | 0.0866 |
| TMLR2DT01 | lymphocytes (non-adher PBMNC), M/F, 24-hr MLR | 4 | 0.0848 |
| ENDCNOT03 | endothelial cells, neonatal M | 4 | 0.0838 |
| MYOMNOT01 | uterus, myometrium, 43 F | 2 | 0.0818 |
| CONNTUT01 | skull tumor, chondroid chordoma, 30 F | 3 | 0.0812 |
| LUNGNOT03 | lung, 79 M, match to LUNGTUT02 | 4 | 0.0801 |
| LATRNOT01 | heart, left atrium, 51 F | 3 | 0.0798 |
| COLNNOT09 | colon, 60 M | 2 | 0.0781 |
| CRBLNOT01 | brain, cerebellum, 69 M | 4 | 0.0781 |
| PGANNON02 | paraganglionic tumor, benign, 46 M, NORM | 1 | 0.0780 |
| THP1NOT03 | THP-1 promonocyte cell line, untreated | 6 | 0.0773 |
| MUSCNOT02 | muscle, psoas, 12 M | 2 | 0.0771 |
| SINTTUT01 | small intestine tumor, ileum, 42 M | 2 | 0.0763 |
| BRAITUT08 | brain tumor, astrocytoma, 47 M | 5 | 0.0733 |
| HEARNOT01 | heart, 56 M | 1 | 0.0713 |
| MMLR2DT01 | macrophages (adher PBMNC), M/F, 48-hr MLR | 4 | 0.0711 |
| PROSTUT03 | prostate tumor, 67 M, match to PROSNOT05 | 2 | 0.0704 |
| SYNORAT04 | synovium, wrist, rheumatoid, 62 F | 4 | 0.0697 |
| SINTNOT02 | small intestine, 55 F | 2 | 0.0692 |
| BRAINON01 | brain, 26 M, NORM | 7 | 0.0691 |
| BRSTTUT03 | breast tumor, 58 F, match to BRSTNOT05 | 7 | 0.0690 |

FIGURE 4B

| | | | |
|---|---|---|---|
| THYRNOT01 | thyroid, 64 F | 3 | 0.0687 |
| ADRENOT03 | adrenal gland, 17 M | 2 | 0.0682 |
| BRSTNOT05 | breast, 58 F, match to BRSTTUT03 | 9 | 0.0672 |
| PLACNOT02 | placenta, fetal F | 4 | 0.0672 |
| PROSNOT20 | prostate, 65 M, match to PROSTUT12 | 2 | 0.0671 |
| PLACNOM02 | placenta, neonatal F, NORM, WM | 12 | 0.0667 |
| MMLR3DT01 | macrophages (adher PBMNC), M/F, 72-hr tmt | 2 | 0.0664 |
| COLNTUT02 | colon tumor, 75 M, match to COLNNOT01 | 3 | 0.0661 |
| COLNNOT13 | colon, ascending, 28 M | 2 | 0.0621 |
| BRAINOT12 | brain, right frontal, epilepsy, 5 M | 2 | 0.0607 |
| ENDCNOT02 | endothelial cells, 30 F | 1 | 0.0604 |
| SCORNOT01 | spinal cord, 71 M | 3 | 0.0603 |
| CONNNOT01 | fat, mesentery, 71 M | 4 | 0.0595 |
| TONGTUT01 | tongue tumor, carcinoma, 36 M | 2 | 0.0590 |
| BRSTNOT07 | breast, 43 F | 4 | 0.0585 |
| NGANNOT01 | ganglioneuroma, 9 M | 8 | 0.0585 |
| PANCNOT05 | pancreas, 2 M | 4 | 0.0583 |
| HNT2AGT01 | hNT2 cell line, post-mitotic neurons | 3 | 0.0576 |
| PROSNOT05 | prostate, 67 M, match to PROSTUT03 | 1 | 0.0576 |
| THP1NOT01 | THP-1 promonocyte cell line, untreated | 1 | 0.0571 |
| LUNGTUT02 | metastatic lung tumor, 79 M | 3 | 0.0567 |
| PROSNOT11 | prostate, 28 M | 2 | 0.0564 |
| SININOT01 | small intestine, ileum, 4 F | 2 | 0.0560 |
| PROSTUT12 | prostate tumor, 65 M, match to PROSNOT20 | 2 | 0.0559 |
| THYRNOT03 | thyroid tumor, adenoma, 28 F | 4 | 0.0553 |
| SINTNOT13 | small intestine, ulcerative colitis, 25 F | 2 | 0.0551 |
| SEMVNOT01 | seminal vesicle, 58 M | 2 | 0.0544 |
| SYNOOAT01 | synovium, knee, osteoarthritis, 82 F | 3 | 0.0539 |
| UTRSNOT08 | uterus, endometrium, 35 F | 2 | 0.0534 |
| PENITUT01 | penis tumor, carcinoma, 64 M | 2 | 0.0533 |
| PROSTUT08 | prostate tumor, 60 M, match to PROSNOT14 | 2 | 0.0532 |
| LUNGNOT10 | lung, fetal M | 2 | 0.0522 |
| CONUTUT01 | mesentery tumor, sigmoid, 61 F | 4 | 0.0520 |
| LUNGNOT14 | lung, 47 M | 2 | 0.0519 |
| PROSNOT18 | prostate, 58 M | 2 | 0.0513 |
| HEARFET01 | heart, fetal M | 2 | 0.0508 |
| PANCNOT08 | pancreas, 65 F, match to PANCTUT01 | 2 | 0.0508 |
| SINTBST01 | small intestine, ileum, Crohn's, 18 F | 3 | 0.0505 |
| TMLR3DT02 | lymphocytes (non-adher PBMNC), 72-hr MLR | 2 | 0.0492 |
| THP1PEB01 | THP-1 promonocyte cell line, treated PMA | 1 | 0.0488 |
| PROSNOT15 | prostate, 66 M, match to PROSTUT10 | 2 | 0.0483 |
| HIPONOT01 | brain, hippocampus, 72 F | 2 | 0.0478 |
| LUNGTUT03 | lung tumor, 69 M, match to LUNGNOT15 | 3 | 0.0478 |
| COLNCRT01 | colon, Crohn's, 40 M, match to COLNNOT05 | 1 | 0.0468 |
| THP1PLB01 | THP-1 promonocyte cell line, tmt PMA, LPS | 1 | 0.0452 |
| CARDNOT01 | heart, 65 M | 1 | 0.0404 |
| TESTNOT03 | testis, 37 M | 3 | 0.0387 |
| HNT3AZT01 | hNT2 cell line, treated AZ | 2 | 0.0381 |
| BLADTUT04 | bladder tumor, 60 M, match to BLADNOT05 | 3 | 0.0380 |
| SPLNFET02 | spleen, fetal M | 3 | 0.0379 |
| THP1AZT01 | THP-1 promonocyte cell line, treated AZ | 2 | 0.0369 |
| STOMTUT01 | stomach tumor, 52 M, match to STOMNOT02 | 1 | 0.0368 |
| PLACNOM03 | placenta, fetal, NORM, WM | 1 | 0.0363 |
| BRAINOT04 | brain, choroid plexus, hemorrhage, 44 M | 1 | 0.0356 |

FIGURE 4C

| | | | |
|---|---|---|---|
| PROSNOT01 | prostate, 78 M | 1 | 0.0351 |
| PROSNOT06 | prostate, 57 M, match to PROSTUT04 | 3 | 0.0343 |
| LVENNOT03 | heart, left ventricle, 31 M | 1 | 0.0339 |
| HIPONON01 | brain, hippocampus, 72 F, NORM | 1 | 0.0338 |
| PANCNOT04 | pancreas, 5 M | 2 | 0.0338 |
| LNODNOT02 | lymph nodes, 42 F | 1 | 0.0335 |
| THP1NOB01 | THP-1 promonocyte cell line, control | 1 | 0.0328 |
| LPARNOT02 | parotid gland, 70 M | 1 | 0.0324 |
| LUNGNOT20 | lung, 61 M | 1 | 0.0309 |
| BLADTUT02 | bladder tumor, 80 F, match to BLADNOT03 | 1 | 0.0305 |
| COLNNOT27 | large intestine, cecum, Crohn's, 31 M | 1 | 0.0303 |
| STOMNOT01 | stomach, 55 M | 1 | 0.0303 |
| BRSTNOT03 | breast, 54 F, match to BRSTTUT02 | 2 | 0.0294 |
| COLNTUT06 | large intestine, cecal tumor, 45 F | 1 | 0.0293 |
| FIBRSEM01 | fibroblasts, senescent, NORM, WM | 1 | 0.0289 |
| DUODNOT01 | small intestine, duodenum, 41 F | 1 | 0.0287 |
| BRAINOT09 | brain, fetal M | 3 | 0.0280 |
| BLADNOT04 | bladder and seminal vesicle, 28 M | 1 | 0.0278 |
| THYRTUT03 | thyroid tumor, benign, 17 M | 1 | 0.0276 |
| HYPONOB01 | hypothalamus, 16-75 M/F | 1 | 0.0272 |
| BLADNOT03 | bladder, 80 F, match to BLADTUT02 | 1 | 0.0271 |
| ENDCNOT01 | endothelial cells, coronary artery, 58 M | 1 | 0.0268 |
| PROSTUT10 | prostate tumor, 66 M, match to PROSNOT15 | 1 | 0.0268 |
| BLADNOT06 | bladder, 66 M, match to BLADTUT05 | 1 | 0.0267 |
| KIDNNOT09 | kidney, fetal M | 1 | 0.0267 |
| BLADNOT05 | bladder, 60 M, match to BLADTUT04 | 1 | 0.0264 |
| LEUKNOT03 | white blood cells, 27 F | 1 | 0.0262 |
| URETTUT01 | ureter tumor, 69 M | 1 | 0.0262 |
| BRAITUT07 | brain tumor, left frontal, 32 M | 1 | 0.0259 |
| LIVRTUT01 | liver tumor, metastasis, 51 F | 1 | 0.0259 |
| PANCTUT02 | pancreatic tumor, carcinoma, 45 F | 3 | 0.0258 |
| ENDANOT01 | endothelial cells, aorta, M | 2 | 0.0257 |
| ISLTNOT01 | pancreas, islet cells, M/F | 4 | 0.0257 |
| SKINBIT01 | skin, leg, erythema nodosum | 1 | 0.0256 |
| BRSTNOT09 | breast, 45 F, match to BRSTTUT08 | 1 | 0.0255 |
| UCMCL5T01 | mononuclear cells, treated IL-5 | 3 | 0.0253 |
| MMLR1DT01 | macrophages (adher PBMNC), M/F, 24-hr MLR | 1 | 0.0236 |
| TMLR3DT01 | lymphocytes (non-adher PBMNC), M, 96-hr MLR | 1 | 0.0229 |
| BRSTNOT02 | breast, 55 F, match to BRSTTUT01 | 2 | 0.0222 |
| SPLNNOT02 | spleen, 29 M | 1 | 0.0220 |
| PANCNOT01 | pancreas, 29 M | 1 | 0.0214 |
| COLNNOT01 | colon, 75 M, match to COLNTUT02 | 1 | 0.0213 |
| COLNNOT16 | colon, sigmoid, 62 M, match to COLNTUT03 | 1 | 0.0208 |
| CORPNOT02 | brain, corpus callosum, Alzheimer's, 74 M | 2 | 0.0205 |
| UTRPNOM01 | uterus, F, NORM, WM | 1 | 0.0201 |
| MELANOM01 | melanocytes, M, NORM, WM | 2 | 0.0192 |
| ADENINB01 | adenoid, inflamed, 3y | 1 | 0.0190 |
| BRAINOM01 | brain, infant F, NORM, WM | 4 | 0.0178 |
| BRAITUT01 | brain tumor, oligoastrocytoma, 50 F | 1 | 0.0134 |
| SPLNNOT04 | spleen, 2 M | 1 | 0.0128 |

FIGURE 4D

HUMAN INTEGRAL MEMBRANE PROTEIN

FIELD OF THE INVENTION

This invention relates to nucleic acid and amino acid sequences of a novel integral membrane protein, IMP-2, and to the use of these sequences in the diagnosis, prevention, and treatment of disease.

BACKGROUND OF THE INVENTION

Membrane proteins are divided into two groups based upon the ease with which the proteins can be removed from the membrane. Extrinsic or peripheral membrane proteins can be removed using extremes of ionic strength or pH, the use of urea or other disruptors of protein interactions. Intrinsic or integral membrane proteins are released only when the lipid bilayer of the membrane is dissolved by detergent. Extrinsic membrane proteins comprise the constituents of the cytoskeleton such as spectrin and actin. Many cytoskeletal proteins are bound directly to integral membrane proteins or are bound indirectly via other proteins such as ankyrin. Cytoskeletal proteins control the shape and dynamics of the cell membrane through their interactions with motor proteins such as myosin and dynein.

The majority of known integral membrane proteins are transmembrane proteins which comprise an extracellular, a transmembrane, and an intracellular domain. Transmembrane proteins are typically embedded into the cell membrane by one or more regions comprising 15 to 25 hydrophobic amino acids which are predicted to adopt an α-helical conformation. Transmembrane proteins are classified as bitopic (or Types I and II) and polytopic (or Types III and IV) [Singer, S. J. (1990) Annu. Rev. Cell Biol. 6:247–96]. Bitopic proteins span the membrane once while polytopic proteins contain multiple membrane-spanning segments. A small number of integral membrane proteins, termed monotopic proteins, are partially embedded in the membrane (i.e., they do not span the lipid bilayer). Monotopic proteins may be inserted into the bilayer by a hydrophobic hairpin loop or may be attached to the membrane via bound lipid.

Type II integral membrane proteins have a single transmembrane stretch of hydrophobic residues which is often located near the amino-terminus. The bulk of type II proteins comprises the carboxy-terminal domain which is located on the exterior side of the cell. The amino-terminal domain of type II proteins, located on the cytoplasmic side of the cell membrane, is typically small. Thus, the type II proteins generally lack enzymatically active domains on the cytoplasmic side of the membrane and thus are not themselves directly involved in transmembrane signalling. The carboxy-terminus of type II proteins typically comprises the active portion of the protein (e.g., the active site of an enzyme, the binding domain of a receptor).

Recently a multigene family encoding type II integral membrane proteins, termed the E25 gene family, was identified [Deleersnijder W. et al. (1996) J. Biol. Chem. 271:19475]. The best characterized member of this family is the mouse Itm2 gene which encodes the E25AMM protein. The expression of the Itm2 gene was found to be associated with chondro-osteogenic differentiation. The Itm2 gene is strongly, although not exclusively, expressed in osteogenic tissue. In particular, Itm2 is strongly expressed in mature osteoblasts and in early stages of secondary chondrogenesis. Itm2 expression is not limited to chondro-osteogenic tissues as it is expressed in 1) heart, brain (choroid plexus), renal cortex, and the crypts of the small intestine (weak expression) and in 2) skin (stratum corneum), hair follicles and the acini of exocrine glands (strong expression) [Deleersnijder W et al., supra]. Additional members of the E25 multigene family have been identified in the mouse and in humans. These additional E25 family members are expressed in a wide variety of tissues including adult and fetal brain, fetal liver, fetal spleen, lung, breast, placenta, prostate, adrenal gland, white blood cells and adult and fetal heart [Deleersnijder W et al., supra].

The discovery of molecules related to the E25 multigene family satisfies a need in the art by providing new diagnostic or therapeutic compositions useful in the treatment of disorders associated with alterations in the expression of members of the E25 multigene family.

SUMMARY OF THE INVENTION

The present invention features a novel integral membrane protein hereinafter designated IMP-2 and characterized as having similarity to the mouse E25AMM integral membrane protein.

Accordingly, the invention features a substantially purified polypeptide having the amino acid sequence shown in SEQ ID NO:1 or fragments thereof. Preferred fragments of SEQ ID NO:1 are fragments of about 15 amino acids or greater in length which define fragments unique (i.e., having less than about 25% identity to fragments of another protein) to SEQ ID NO:1 or which retain biological activity or immunological activity (i.e., capable of eliciting anti-IMP-2 antibodies). Fragments of SEQ ID NO:1 which are at least 25 amino acids, at least 50 amino acids, at least 100 amino acids, at least 125 amino acids and at least 200 amino acids in length are contemplated.

The present invention further provides isolated and substantially purified polynucleotide sequences encoding the polypeptide comprising the amino acid sequence of SEQ ID NO:1 or fragments thereof. In a particular aspect, the polynucleotide is the nucleotide sequence of SEQ ID NO:2 or variants thereof. In another embodiment, the present invention provides polynucleotides comprising fragments of SEQ ID NO:2 having a length greater than 20 nucleotides. The invention further contemplates fragments of this polynucleotide sequence (i.e., SEQ ID NO:2) that are at least 50 nucleotides, at least 100 nucleotides, at least 250 nucleotides, at least 500 nucleotides and at least 1000 nucleotides in length.

In addition, the invention provides polynucleotide sequences which hybridize under stringent conditions to the polynucleotide sequence of SEQ ID NO:2. In another embodiment the present invention provides a composition comprising an isolated and purified polynucleotide sequence encoding IMP-2.

The invention provides polynucleotide sequences comprising the complement of SEQ ID NO:2 or variants thereof, these complementary nucleic acid sequences may comprise the complement of the entire nucleic acid sequence of SEQ ID NO:2 or fragments thereof. In another embodiment the present invention provides a composition comprising an isolated and purified polynucleotide sequence comprising the complement of SEQ ID NO:2 or variants thereof.

The invention additionally features nucleic acid sequences encoding polypeptides, oligonucleotides, peptide nucleic acids (PNA), fragments, portions or antisense molecules thereof, and expression vectors and host cells comprising polynucleotides that encode IMP-2.

In another embodiment the present invention provides an isolated polynucleotide comprising at least a portion of the nucleic acid sequence of SEQ ID NO:2 or variants thereof contained on a recombinant expression vector. In yet another embodiment, the expression vector containing the polynucleotide sequence is contained within a host cell. The invention is not limited by the nature of the host cell employed. For example, the host cell may be an *E. coli* cell, a yeast cell, an insect cell, a mammalian cell, etc.

The present invention also provides a method for producing a polypeptide comprising the amino acid sequence of SEQ ID NO:1 or fragments thereof, the method comprising the steps of: a) culturing the host cell containing an expression vector containing an isolated polynucleotide encoding at least a fragment of the IMP-2 polypeptide under conditions suitable for the expression of the polypeptide; and b) recovering the polypeptide from the host cell culture.

In another embodiment, the invention provides a pharmaceutical composition comprising a substantially purified human IMP-2 protein having the amino acid sequence of SEQ ID NO:1 in conjunction with a suitable pharmaceutical carrier.

The invention also provides a purified antibody which binds specifically to a polypeptide comprising at least a portion of the amino acid sequence of SEQ ID NO:1.

Still further, the invention provides a purified agonist which specifically binds to and modulates the activity of a polypeptide comprising at least a portion of the amino acid sequence of SEQ ID NO:1. The present invention further provides a pharmaceutical composition comprising a purified agonist which specifically binds to and modulates the activity of a polypeptide comprising at least a portion of the amino acid sequence of SEQ ID NO:1. In another embodiment, the invention provides a purified antagonist which specifically binds to and modulates the activity of a polypeptide comprising at least a portion of the amino acid sequence of SEQ ID NO:1. The present invention further provides a pharmaceutical composition comprising a purified antagonist which specifically binds to and modulates the activity of a polypeptide comprising at least a portion of the amino acid sequence of SEQ ID NO:1.

The invention also provides a method for treating liver disease (including liver tumors) comprising administering to a subject in need of such treatment an effective amount of a pharmaceutical composition comprising a purified agonist which specifically binds to and modulates the activity of a polypeptide comprising at least a portion of the amino acid sequence of SEQ ID NO:1. The treatment of a variety of tumors, including but not limited to tumors of the lung, prostate, breast and bladder, using agonists as well as antagonists of IMP-2 is also contemplated by the present invention.

The invention also provides a method for detection of polynucleotides encoding human IMP-2 in a biological sample comprising the steps of: a) hybridizing a polynucleotide sequence encoding human IMP-2 (SEQ ID NO:1) to nucleic acid material of a biological sample, thereby forming a hybridization complex; and b) detecting the hybridization complex, wherein the presence of the complex correlates with the presence of a polynucleotide encoding human IMP-2 in the biological sample. In a preferred embodiment, prior to hybridization, the nucleic acid material of the biological sample is amplified by the polymerase chain reaction.

BRIEF DESCRIPTION OF THE FIGURES

FIGS. 1B and 1C show the amino acid sequence (SEQ ID NO:1) and nucleic acid sequence (SEQ ID NO:2) of IMP-2. The alignment was produced using MACDNASIS PRO™ software (Hitachi Software Engineering Co., Ltd., San Bruno, Calif.).

FIG. 2A and 2B shows the amino acid sequence alignments among IMP-2 (SEQ ID NO:1) and E25AMM (GI 624778; SEQ ID NO:3). The alignment was produced using the multisequence alignment program of DNASTAR™ software (DNASTAR Inc, Madison Wis.).

FIGS. 4A, 4B, 4C, and 4D show the northern analysis for SEQ ID NO:2. The northern analysis was produced electronically using LIFESEQ™ database (Incyte Pharmaceuticals, Inc., Palo Alto, Calif.).

DESCRIPTION OF THE INVENTION

Figure 3A:
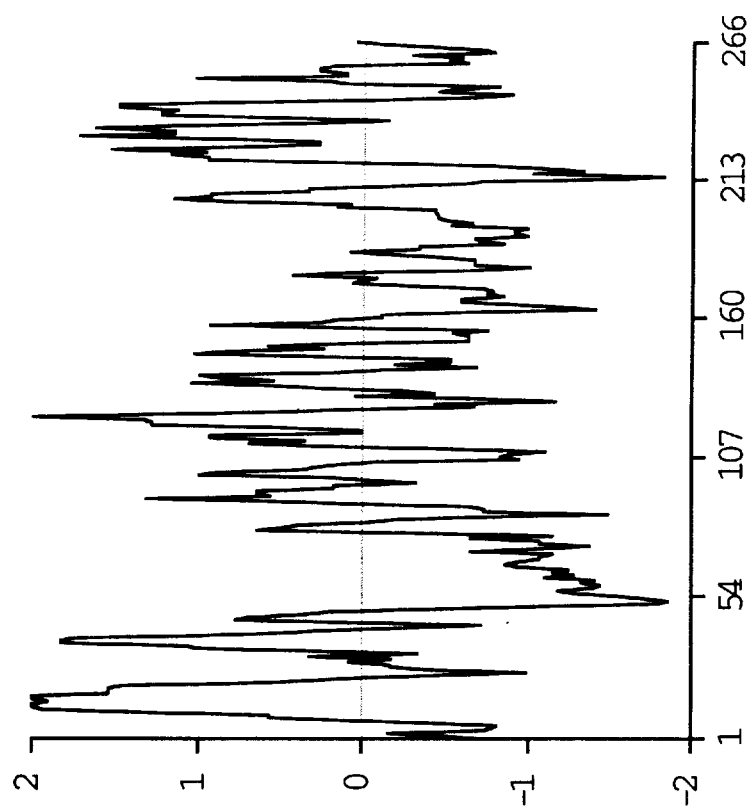
FIGS. 3A and 3B show the hydrophobicity plots (MacDNASIS PRO software) for IMP-2, (SEQ ID NO:1) and E25AMM (SEQ ID NO:3); the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

A "composition comprising a given polynucleotide sequence", as used herein, refers broadly to any composition containing the given polynucleotide sequence. The composition may comprise an aqueous solution. Compositions comprising polynucleotide sequences encoding IMP-2 (SEQ ID NO:1) or fragments thereof (e.g., SEQ ID NO:2 and fragments thereof) may be employed as hybridization probes. In this case, the IMP-2-encoding polynucleotide sequences are typically employed in an aqueous solution containing salts (e.g., NaCl), detergents (e.g., SDS) and other components (e.g., Denhardt's solution, dry milk, salmon sperm DNA, etc.).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

IMP-2, as used herein, refers to the amino acid sequences of substantially purified IMP-2 obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of IMP-2, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic IMP-2, or any oligopeptide thereof, to induce a specific immune response in appropriate animals or cells and to bind with specific antibodies.

The term "agonist", as used herein, refers to a molecule which, when bound to IMP-2, causes a change in IMP-2 which modulates the activity of IMP-2. Agonists may include proteins, nucleic acids, carbohydrates, or any other molecules which bind to IMP-2.

The terms "antagonist" or "inhibitor", as used herein, refer to a molecule which, when bound to IMP-2, blocks or modulates the biological or immunological activity of IMP-2. Antagonists and inhibitors may include proteins, nucleic acids, carbohydrates, or any other molecules which bind to IMP-2.

The term "modulate", as used herein, refers to a change or an alteration in the biological activity of IMP-2. Modulation may be an increase or a decrease in protein activity, a change in binding characteristics, or any other change in the biological, functional, or immunological properties of IMP-2.

The term "mimetic", as used herein, refers to a molecule, the structure of which is developed from knowledge of the structure of IMP-2 or portions thereof and, as such, is able to effect some or all of the actions of IMP-2-like molecules.

The term "derivative", as used herein, refers to the chemical modification of a nucleic acid encoding IMP-2 or the encoded IMP-2. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences. Under "stringent conditions" SEQ ID NO:2 or fragments thereof will hybridize to its exact complement and closely related sequences. The stringent conditions are chosen such that SEQ ID NO:2 or fragments thereof will hybridize to sequences encoding human IMP-2 but not to sequences encoding mouse E25AMM (i.e., SEQ ID NO:4 or its RNA equivalents). When fragments of SEQ ID NO:2 are employed in hybridization reactions, the stringent conditions include the choice of fragments of SEQ ID NO:2 to be used. Fragments of SEQ ID NO:2 which contain unique sequences (i.e., regions which are either non-homologous to or which contain less than about 50% homology or complementarity with SEQ ID NO:4) are preferentially employed. SEQ ID NO:4 represents DNA sequences encoding the mouse E25AMM protein; this DNA sequence can be found in GenBank under accession number 624778.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human IMP-2 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding IMP-2 or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding IMP-2 in a sample and thereby correlates with expression of the transcript from the polynucleotide encoding the protein.

"Alterations" in the polynucleotide of SEQ ID NO:2, as used herein, comprise any alteration in the sequence of polynucleotides encoding IMP-2 including deletions, insertions, and point mutations that may be detected using hybridization assays. Included within this definition is the detection of alterations to the genomic DNA sequence which encodes IMP-2 (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding IMP-2 (e.g., using fluorescent in situ hybridization [FISH] to metaphase chromosome spreads).

As used herein, the term "antibody" refers to intact molecules as well as fragments thereof, such as Fa, F(ab')$_2$, and Fv, which are capable of binding the epitopic determinant. Antibodies that bind IMP-2 polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a novel human integral membrane protein (IMP-2), the polynucleotides encoding IMP-2, and the use of these compositions for the diagnosis, prevention, or treatment of diseases associated with abnormal liver tissue, including liver tumors. In addition, as mRNA encoding IMP-2 is found in a number of other tumors, IMP-2 serves as a marker for cancerous cells, particularly brain, prostate, breast and bladder tumor cells.

Nucleic acids encoding the human IMP-2 of the present invention were first identified in Incyte Clone 632664 from the NEUTGMT01 cDNA library through a computer-generated search for amino acid sequence alignments. A consensus sequence, SEQ ID NO:2, was derived from the following overlapping and/or extended nucleic acid sequences: Incyte Clones 436536 (THYRNOT01), 632664 (NEUTGMT01), 1301662 (BRSTNOT07), 2278468 (PROSNON01), and 2353669 (LUNGNOT20).

In one embodiment, the invention encompasses a polypeptide comprising the amino acid sequence of SEQ ID NO:1, as shown in FIGS. 1A and 1B. IMP-2 is 266 amino acids in length and contains nine cysteine residues (i.e., $C_{38}$, $C_{54}$, $C_{56}$, $C_{57}$, $C_{89}$, $C_{164}$, $C_{223}$, $C_{248}$, and $C_{265}$). In addition to providing sites for disulfide bond formation, the cysteine residues provide potential sites for palmitoylation. Five of the nine cysteine residues found in human IMP-2 are conserved in location with cysteine residues found in the mouse E25AMM protein (i.e., $C_{56}$, $C_{164}$, $C_{223}$, $C_{248}$, and $C_{265}$ of IMP-2). The human IMP-2 of the present invention contains numerous potential O-linked glycosylation sites (i.e., serine and threonine residues). IMP-2 has a single potential N-linked glycoslyation site (i.e., Asn-X-Ser/Thr) (i.e., $N_{170}$) which is conserved in location with the single N-linked glycoslyation site found in the mouse E25AMM protein (Deleersnijder et al., supra). In addition, the human IMP-2 of the present invention contains numerous potential phosphorylation sites (i.e., typically the hydroxyl groups of serine, threonine and tyrosine residues although asparagine, histidine and lysine residues may also be phosphorylated), including a potential site for phosphorylation by cAMP-dependent protein kinase (e.g., R-X-S/T) (i.e., $T_{236}$).

The IMP-2 protein of the present invention, like the mouse E25AMM protein, has an acidic isoelectric point (pI) (IMP-2 has a pI of 4.86 and E25AMM has a pI of 5.41). In addition, the IMP-2 protein of the present invention, like the mouse E25AMM protein, has a high content of leucine and isoleucine residues (IMP-2 contains 9% leucine and 9% isoleucine; E25AMM contains 10.2% leucine and 8% isoleucine).

Figure 3B:
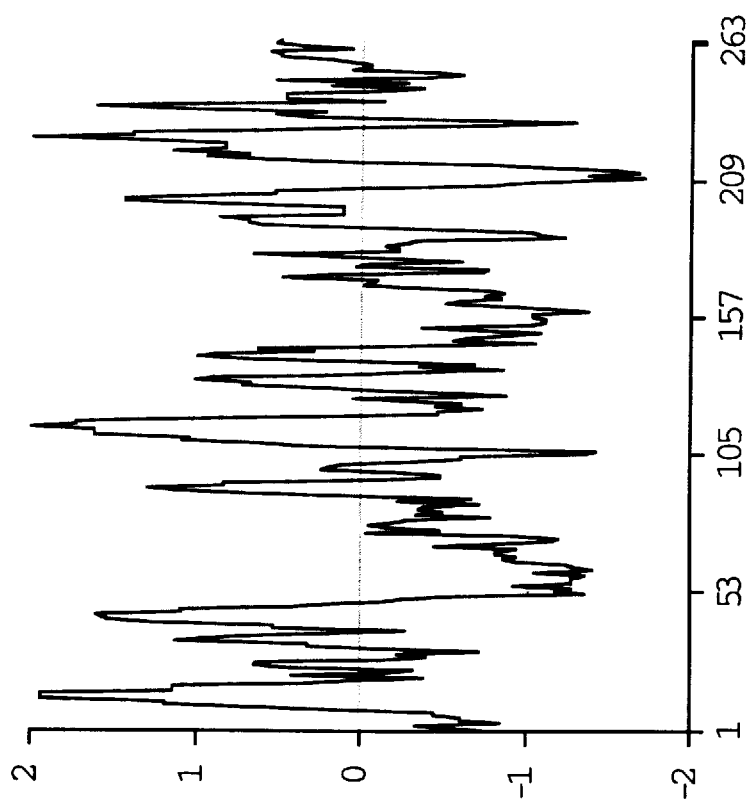

IMP-2 contains a stretch of hydrophobic amino acid residues at positions 53–76 which presumably forms the membrane spanning domain. As illustrated by FIGS. 3A and 3B and FIGS. 4A, 4B, 4C and 4D, IMP-2 and E25AMM have similar hydrophobicity plots.

IMP-2 has chemical and structural homology with the mouse E25AMM protein (GI 624778; SEQ ID NO:3) (Deleersnijder et al., supra). In particular, IMP-2 and E25AMM share 39.8% identity overall and 49% identity and 71% similarity over the carboxy-terminal domians (residues 115–265 of IMP-2 and residues 111–261 of E25AMM). A pair of residues are said to be similar if they represent conservative substitutions. FIG. 2 provides an alignment between the amino acid sequences of SEQ ID NOS: 1 and 3.

Northern analysis shows the expression of IMP-2-encoding sequences in various libraries, at least 24% of which are cancerous or immortalized and at least 17% of which are involved with the immune response, including inflammatory and/or autoimmune disease (e.g., rheumatoid synovium, ulcerative colitis, Crohn's disease, primary biliary cirrhosis). Of particular note is the expression of IMP-2 mRNA in brain tumor (7/214), prostate tumor (6/214), breast tumor (3/214) and bladder tumor (3/214) libraries. This pattern of expression demonstrates that IMP-2 serves as a marker for cancerous cells, particularly brain and prostate tumor cells. In addition to its expression in a variety of tumors, IMP-2 is highly expressed in adult liver and fetal spleen and thus serves as a marker for these tissues.

IMP-2 cDNA is strongly expressed in normal adult liver (>10% abundance; see LIVRNOT01 and LIVRNOM01 libraries) and its expression decreases precipitously in abnormal liver tissues, including primary biliary cirrhosis (see LIVRBCT01 library; 3.5% abundance) and liver tumors (see LIVRTUT01 library; 0.03% abundance). Thus, decreased or low level (i.e., less than about 50% the level seen in normal or disease-free, liver tissue) expression of IMP-2 in liver tissue serves as an indicator of liver disease, including liver cancer. A similar decrease in IMP-2 transcripts is observed when normal lung and lung tumors are compared; lung tumors show about a 50% decrease in IMP-2 transcript abundance as compared to normal adult lung. Thus, decreased or low level expression of IMP-2 in lung tissue serves as an indicator of lung tumors.

The invention also encompasses IMP-2 variants. A preferred IMP-2 variant is one having at least 80%, and more preferably 90%, amino acid sequence similarity to the IMP-2 amino acid sequence (SEQ ID NO:1). A most preferred IMP-2 variant is one having at least 95% amino acid sequence similarity to SEQ ID NO:1.

The invention also encompasses polynucleotides which encode IMP-2. Accordingly, any nucleic acid sequence which encodes the amino acid sequence of IMP-2 can be used to generate recombinant molecules which express IMP-2. In a particular embodiment, the invention encompasses the polynucleotide comprising the nucleic acid sequence of SEQ ID NO:2 as shown in FIGS. 1A and 1B.

It will be appreciated by those skilled in the art that as a result of the degeneracy of the genetic code, a multitude of nucleotide sequences encoding IMP-2, some bearing minimal homology to the nucleotide sequences of any known and naturally occurring gene, may be produced. Thus, the invention contemplates each and every possible variation of nucleotide sequence that could be made by selecting combinations based on possible codon choices.

These combinations are made in accordance with the standard triplet genetic code as applied to the nucleotide sequence of naturally occurring IMP-2, and all such variations are to be considered as being specifically disclosed.

Although nucleotide sequences which encode IMP-2 and its variants are preferably capable of hybridizing to the nucleotide sequence of the naturally occurring IMP-2 under appropriately selected conditions of stringency, it may be advantageous to produce nucleotide sequences encoding IMP-2 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding IMP-2 and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode IMP-2 and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding IMP- or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding IMP-2 which are encompassed by the invention include deletions, insertions, or substitutions of different nucleotides resulting in a polynucleotide that encodes the same or a functionally equivalent IMP-2. The encoded protein may also contain deletions, insertions, or substitutions of amino acid residues which produce a silent change and result in a functionally equivalent IMP-2. Deliberate amino acid substitutions may be made on the basis of similarity in polarity, charge, solubility, hydrophobicity, hydrophilicity, and/or the amphipathic nature of the residues as long as the biological activity of IMP-2 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding IMP-2. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE® (U.S. Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding IMP-2 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic.

1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTER FINDER™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode IMP-2, or fusion proteins or functional equivalents thereof, may be used in recombinant DNA molecules to direct expression of IMP-2 in appropriate host cells. Due to the inherent degeneracy of the genetic code, other DNA sequences which encode substantially the same or a functionally equivalent amino acid sequence may be produced and these sequences may be used to clone and express IMP-2.

As will be understood by those of skill in the art, it may be advantageous to produce IMP-2-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter IMP-2 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding IMP-2 may be ligated to a heterologous sequence to encode a fusion protein. For example, to screen peptide libraries for inhibitors of IMP-2 activity, it may be useful to encode a chimeric IMP-2 protein that can be recognized by a commercially available antibody. A fusion protein may also be engineered to contain a cleavage site located between the IMP-2 encoding sequence and the heterologous protein sequence, so that IMP-2 may be cleaved and purified away from the heterologous moiety.

In another embodiment, sequences encoding IMP-2 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of IMP-2, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of IMP-2, or any part thereof, may be altered during direct synthesis and/or combined using chemical methods with sequences from other proteins, or any part thereof, to produce a variant polypeptide.

In order to express a biologically active IMP-2, the nucleotide sequences encoding IMP-2 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding IMP-2 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding IMP-2. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding IMP-2, vectors based on SV40 or EBV may be used with an appropriate selectable marker.

In bacterial systems, a number of expression vectors may be selected depending upon the use intended for IMP-2. For example, when large quantities of IMP-2 are needed for the induction of antibodies, vectors which direct high level expression of fusion proteins that are readily purified may be used. Such vectors include, but are not limited to, the multifunctional E. coli cloning and expression vectors such as BLUESCRIPT® (Stratagene), in which the sequence encoding IMP-2 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding IMP-2 may be driven by any of a number of promotors. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196.

An insect system may also be used to express IMP-2. For example, in one such system, Autographa californica nuclear polyhedrosis virus (AcNPV) is used as a vector to express foreign genes in Spodoptera frugiperda cells or in Trichoplusia larvae. The sequences encoding IMP-2 may be cloned into a non-essential region of the virus, such as the polyhedrin gene, and placed under control of the polyhedrin promoter. Successful insertion of IMP-2 will render the polyhedrin gene inactive and produce recombinant virus lacking coat protein. The recombinant viruses may then be used to infect, for example, S. frugiperda cells or Trichoplusia larvae in which IMP-2 may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding IMP-2 may be ligated into an adenovirus transcription/translation complex consisting of the late promoter and tripartite leader sequence. Insertion in a non-essential E1 or E3 region of the viral genome may be used to obtain a viable virus which is capable of expressing IMP-2 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding IMP-2. Such signals include the ATG initiation codon and adjacent sequences. In cases where sequences encoding IMP-2, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO (ATCC CCL 61 and CRL 9618), HeLa (ATCC CCL 2), MDCK (ATCC CCL 34 and CRL 6253), HEK 293 (ATCC CRL 1573), WI-38 (ATCC CCL 75) (ATCC: American Type Culture Collection, Rockville, Md.), which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express IMP-2 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, βglucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding IMP-2 is inserted within a marker gene sequence, recombinant cells containing sequences encoding IMP-2 can be identified by the absence of marker gene function. Alternatively, a marker gene can be placed in tandem with a sequence encoding IMP-2 under the control of a single promoter. Expression of the marker gene in response to induction or selection usually indicates expression of the tandem gene as well.

Alternatively, host cells which contain the nucleic acid sequence encoding IMP-2 and express IMP-2 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding IMP-2 can be detected by DNA-DNA or DNA-RNA hybridization or amplification using probes or portions or fragments of polynucleotides encoding IMP-2. Nucleic acid amplification based assays involve the use of oligonucleotides or oligomers based on the sequences encoding IMP-2 to detect transformants containing DNA or RNA encoding IMP-2. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of IMP-2, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on IMP-2 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding IMP-2 include oligolabeling, nick translation, end-labeling or PCR amplification using a labeled nucleotide. Alternatively, the sequences encoding IMP-2, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding IMP-2 may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode IMP-2 may be designed to contain signal sequences which direct secretion of IMP-2 through a prokaryotic or eukaryotic cell membrane. When it is desired to express a secreted form of IMP-2, a polynucleotide sequence encoding a portion of the IMP-2 lacking the hydrophobic stretch located at residues 53–76 of SEQ ID NO:1 (this stretch may anchor IMP-2 in the membrane) is preferentially employed.

Other recombinant constructions may be used to join sequences encoding IMP-2 to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and IMP-2 may be used to facilitate purification. One such expression vector provides for expression of a fusion protein containing IMP-2 and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263–281) while the enterokinase cleavage site provides a means for purifying IMP-2 from the fusion protein. A discussion of vectors which contain fusion proteins is provided in Kroll, D. J. et al. (1993; DNA Cell Biol. 12:441–453).

In addition to recombinant production, fragments of IMP-2 may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431 A Peptide Synthesizer (Perkin Elmer). Various fragments of IMP-2 may be chemically synthesized separately and combined using chemical methods to produce the full length molecule.

Therapeutics

Based on the chemical and structural homology among IMP-2 (SEQ ID NO:1) and the mouse E25AMM protein (SEQ ID NO:3), IMP-2 appears to be a member of the E25 multigene family. E25AMM has been shown to be differentially expressed in bone and cartilage tissue and thus serves as a marker for chondro-osteogenic differentiation (Deleersnijder W. et al., supra). Based on the homology between IMP-2 and E25AMM, IMP- 2 may likewise serve as a marker for bone and cartilage tissue. More importantly, as shown herein, IMP-2 is strongly expressed in normal adult liver and its expression decreases precipitously in abnormal liver tissues, including primary biliary cirrhosis and liver tumors. Thus, decreased or low level (i.e., less than about 50% the level seen in normal or disease-free, liver tissue) expression of IMP-2 in liver tissue serves as an indicator of liver disease, including liver cancer. A similar decrease in IMP-2 transcripts is observed when normal lung and lung tumors are compared; lung tumors show about a 50% decrease in IMP-2 transcript abundance as compared to normal adult lung. IMP-2 is expressed in a variety of other tumor types including brain, prostate, breast and bladder.

Therefore, in one embodiment, IMP-2 or a fragment or derivative thereof may be administered to a subject to treat disorders associated with abnormal liver function as well as a variety of tumors. Such conditions and diseases may include, but are not limited to, liver tumors, primary biliary cirrohsis and lung, brain, prostate, breast and bladder tumors.

In another embodiment, a vector capable of expressing IMP-2, or a fragment or a derivative thereof, may also be administered to a subject to treat the liver tumors, primary biliary cirrohsis and lung, brain, prostate, breast and bladder tumors described above.

In another embodiment, IMP-2 may be administered in combination with other conventional chemotherapeutic agents. The combination of therapeutic agents having different mechanisms of action will have synergystic effects allowing for the use of lower effective doses of each agent and lessening side effects.

In one aspect, agonists of IMP-2 may be used to increase the activity of IMP-2 in cells having reduced IMP-2 levels. Antibodies which are specific for IMP-2 may be used directly as an agonist, or indirectly as a targeting or delivery mechanism for bringing a pharmaceutical agent to cells or tissue which express IMP-2.

In one embodiment, antagonists or inhibitors of IMP-2 may be administered to a subject to treat or prevent tumors, particularly brain, prostate, breast and bladder tumors.

In another embodiment, a vector expressing antisense of the polynucleotide encoding IMP-2 may be administered to a subject to treat or prevent tumors, particularly brain, prostate, breast and bladder tumors.

Antagonists or inhibitors of IMP-2 may be produced using methods which are generally known in the art. In particular, purified IMP-2 may be used to produce antibodies or to screen libraries of pharmaceutical agents to identify those which specifically bind IMP-2.

Antibodies which are specific for IMP-2 may be used directly as an antagonist, or indirectly as a targeting or delivery mechanism for bringing a pharmaceutical agent to cells or tissue which express IMP-2. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which reduce or abolish IMP-2 activity) are especially preferred for therapeutic use.

For the production of antibodies, various hosts including goats, rabbits, rats, mice, humans, and others, may be immunized by injection with IMP-2 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to IMP-2 have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of IMP-2 amino acids may be fused with those of another protein such as keyhole limpet hemocyanin and antibody produced against the chimeric molecule.

Monoclonal antibodies to IMP-2 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce IMP-2-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for IMP-2 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between IMP-2 and its specific antibody. A two-site, monoclonal-based immunoassay utilizing monoclonal antibodies reactive to two non-interfering IMP-2 epitopes is preferred, but a competitive binding assay may also be employed (Maddox, supra).

In another embodiment of the invention, the polynucleotides encoding IMP-2, or any fragment thereof, or antisense molecules, may be used for therapeutic purposes. In one aspect, antisense to the polynucleotide encoding IMP-2 may be used in situations in which it would be desirable to block the transcription of the mRNA. In particular, cells may be transformed with sequences complementary to polynucleotides encoding IMP-2. Thus, antisense molecules may be used to modulate IMP-2 activity, or to achieve regulation of gene function. Such technology is now well known in the art, and sense or antisense oligomers or larger fragments, can be designed from various locations along the coding or control regions of sequences encoding IMP-2.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding IMP-2. These techniques are described both in Sambrook et al. (supra) and in Ausubel et al. (supra).

Genes encoding IMP-2 can be turned off by transforming a cell or tissue with expression vectors which express high levels of a polynucleotide or fragment thereof which encodes IMP-2. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding IMP-2, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding IMP-2.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding IMP-2. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of IMP-2, antibodies to IMP-2, mimetics, agonists, antagonists, or inhibitors of IMP-2. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of IMP-2, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example IMP-2 or fragments thereof, antibodies of IMP-2, agonists, antagonists or inhibitors of IMP-2, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind IMP-2 may be used for the diagnosis of conditions or diseases characterized by expression of IMP-2, or in assays to monitor patients being treated with IMP-2, agonists, antagonists or inhibitors. The antibodies useful for diagnostic purposes may be prepared in the same manner as those described above for therapeutics. Diagnostic assays for IMP-2 include methods which utilize the antibody and a label to detect IMP-2 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring IMP-2 are known in the art and provide a basis for diagnosing altered or abnormal levels of IMP-2 expression. Normal or standard values for IMP-2 expression are established by combining body fluids or cell extracts taken from normal mammalian subjects, preferably human, with antibody to IMP-2 under conditions suitable for complex formation. The amount of standard complex formation may be quantified by various methods, but preferably by photometric means. Quantities of IMP-2 expressed in subject, control, and disease samples from biopsied tissues are compared with the standard values. Deviation between standard and subject values establishes the parameters for diagnosing disease.

In another embodiment of the invention, the polynucleotides encoding IMP-2 is used for diagnostic purposes. The polynucleotides which may be used include oligonucleotide sequences, antisense RNA and DNA molecules, and PNAs. The polynucleotides may be used to detect and quantitate gene expression in biopsied tissues in which expression of IMP-2 may be correlated with disease. The diagnostic assay may be used to distinguish between absence, presence, and excess expression of IMP-2, and to monitor regulation of IMP-2 levels during therapeutic intervention.

In one aspect, hybridization with PCR probes which are capable of detecting polynucleotide sequences, including genomic sequences, encoding IMP-2 or closely related molecules, may be used to identify nucleic acid sequences which encode IMP-2. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding IMP-2, alleles, or related sequences.

Probes may also be used for the detection of related sequences, and should preferably contain at least 50% of the nucleotides from any of the IMP-2 encoding sequences. The hybridization probes of the subject invention may be DNA or RNA and derived from the nucleotide sequence of SEQ ID NO:2 or from genomic sequence including promoter, enhancer elements, and introns of the naturally occurring IMP-2.

Means for producing specific hybridization probes for DNAs encoding IMP-2 include the cloning of nucleic acid sequences encoding IMP-2 or IMP-2 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding IMP-2 may be used for the diagnosis of conditions or diseases which are associated with expression of IMP-2. Examples of such conditions or diseases include cancers of the liver, lung, brain, prostate, breast and bladder and primary biliary cirhorrsis. The polynucleotide sequences encoding IMP-2 may be used in Southern or northern analysis, dot blot, or other membrane-based technologies; in PCR technologies; or in dip stick, pin, ELISA or chip assays utilizing fluids or tissues from patient biopsies to detect altered IMP-2 expression. Such qualitative or quantitative methods are well known in the art.

In a particular aspect, the nucleotide sequences encoding IMP-2 provide the basis for assays that detect activation or induction of various cancers, particularly those mentioned above; in addition the lack of expression of IMP-2 may be detected using the IMP-2-encoding nucleotide sequences disclosed herein. The nucleotide sequences encoding IMP-2 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding IMP-2 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of IMP-2, a normal or standard profile for expression is established. This may be accomplished by combining body fluids or cell extracts taken from normal subjects, either animal or human, with a sequence, or a fragment thereof, which encodes IMP-2, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low or a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding IMP-2 may involve the use of PCR. Such oligomers may be chemically synthesized, generated enzymatically, or produced from a recombinant source. Oligomers will preferably consist of two nucleotide sequences, one with sense orientation (5→3') and another with antisense (3→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of IMP-2 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode IMP-2 may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial PI constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981 f). Correlation between the location of the gene encoding IMP-2 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11 q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, IMP-2, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between IMP-2 and the agent being tested, may be measured.

Another technique for drug screening which may be used provides for high throughput screening of compounds having suitable binding affinity to the protein of interest as described in published PCT application WO84/03564. In this method, as applied to IMP-2 large numbers of different small test compounds are synthesized on a solid substrate, such as plastic pins or some other surface. The test compounds are reacted with IMP-2, or fragments thereof, and washed. Bound IMP-2 is then detected by methods well known in the art. Purified IMP-2 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding IMP-2 specifically compete with a test compound for binding IMP-2. In this manner, the antibodies can be used to detect the presence of any peptide which shares one or more antigenic determinants with IMP-2.

In additional embodiments, the nucleotide sequences which encode IMP-2 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I NEUTGMT01 cDNA Library Construction

The NEUTGMT01 library was constructed using 1 microgram of polyA RNA isolated from peripheral blood granulocytes collected by density gradient centrifugation through Ficoll-Hypaque. The cells were isolated from buffy coat units obtained from 20 unrelated male and female donors at the Stanford Blood Bank (Stanford, Calif.). Cells were cultured in 10 nM GM-CSF for 1 hour before harvest.

Cells were lysed in buffer containing guanidinium isothiocyanate. The lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted once with acid phenol at pH 4.0, twice with phenol chloroform at pH 8.0, precipitated using 0.3M sodium acetate and 2.5 volumes of ethanol, resuspended in DEPC-treated water, and DNase treated for 15 min at 37° C. The RNA was isolated with the QIAGEN OLICOTEX kit (QIAGEN Inc, Chatsworth Calif.) and used to construct the cDNA library.

The RNA was handled according to the recommended protocols in the SuperScript Plasmid System for cDNA Synthesis and Plasmid Cloning (Cat#18248-013; Gibco/BRL, Gaitherburg, Md.), and cDNAs were ligated into PSPORT1. The plasmid PSPORT1 was subsequently transformed into DH5aD™ competent cells (Cat# 18258-012, Gibco/BRL).

II Isolation and Sequencing of cDNA Clones

Plasmid DNA was released from the cells and purified using the Miniprep Kit (Cat# 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat# 22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R at 2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS- DNA, QIAwell—8 Plasmid, QlAwell PLUS DNA, and QlAwell ULTRA DNA purification systems (QIAGEN Chatsworth Calif.).

The cDNAs were sequenced by the method of Sanger F. and A. R. Coulson (1975; J Mol Biol 94:441f), using a Hamilton Micro Lab 2200 (Hamilton, Reno, Nev.) in combination with four Peltier Thermal Cyclers (PTC200 from MJ Research, Watertown, Mass.) and Applied Biosystems 377 or 373 DNA Sequencing Systems (Perkin Elmer), and the reading frame was determined.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

A comparison of the full-length and partial cDNA sequences and the deduced amino acid sequences corresponding to the human IMP-2 gene and IMP-2 protein with known nucleotide and protein sequences in GenBank revealed that the full-length human IMP-2 cDNA and protein sequences (i.e., SEQ ID NOS:1 and 2) were unique (i.e., not previously identified). This search revealed that the human IMP-2 protein shared some homology with the mouse E25AMM protein (SEQ ID NO:3), the *Caenorhabditis briggsae* G01D9.4 gene product which is of unknown function (GI 1293791) and the HR21 spa protein which is involved in DNA double-strand break repair (GI 1620398). In addition, portions of the amino acid sequence of IMP-2 were found to share homology with a number of short EST sequences of human origin (GI 1331732, GI 1376262, GI 764606, GI 873070 and GI 864758).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

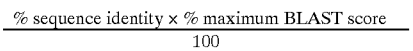

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding IMP-2 occurs. Abundance and percent abundance are also reported. Abundance directly reflects the number of times a particular transcript is represented in a cDNA library, and percent abundance is abundance divided by the total number of sequences examined in the cDNA library.

Electronic northern analysis revealed that mRNA encoding human IMP-2 (SEQ ID NO:1) was present in libraries generated from a wide variety of adult and fetal tissues. IMP-2 cDNA is most strongly expressed in normal adult liver and its expression decreases dramatically in abnormal liver tissues, including primary biliary cirrhosis and liver tumors. In addition to expression in apparently normal human tissues, IMP-2 was expressed in a variety of tumors, including but not limited to brain, prostate, breast and bladder tumors as well as in several immortalized cell lines. IMP-2 cDNA is also expressed in a variety of tissues and cell lines which are involved with the immune response, including inflammatory and/or autoimmune disease (e.g., rheumatoid synovium, ulcerative colitis, Crohn's disease, primary biliary cirrhosis).

V Extension of IMP-2-Encoding Polynucleotides to Full Length or to Recover Regulatory Sequences Full length IMP-2-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

| Step 1  | 94° C. for 1 min (initial denaturation) |
|---------|------------------------------------------|
| Step 2  | 65° C. for 1 min |
| Step 3  | 68° C. for 6 min |
| Step 4  | 94° C. for 15 sec |
| Step 5  | 65° C. for 1 min |
| Step 6  | 68° C. for 7 min |
| Step 7  | Repeat step 4–6 for 15 additional cycles |
| Step 8  | 94° C. for 15 sec |
| Step 9  | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 tide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 370° C., the whole transformation mixture is plated on Luria Bertani (LB)-agar (Sambrook et al., supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
|--------|-------------------|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the IMP-2-encoding sequence, or any part thereof, is used to inhibit in vivo or in vitro expression of naturally occurring IMP-2. Although use of antisense oligonucleotides, comprising about 20 base-pairs, is specifically described, essentially the same procedure is used with larger cDNA fragments. An oligonucleotide based on the coding sequences of IMP-2, as shown in FIGS. 1A and 1B, is used to inhibit expression of naturally occurring IMP-2. The complementary oligonucleotide is designed from the most unique 5' sequence as shown in FIGS. 1AA and 1B and used either to inhibit transcription by preventing promoter binding to the upstream nontranslated sequence or translation of an IMP-2-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A and 1B.

VIII Expression of IMP-2

Expression of IMP-2 is accomplished by subcloning the cDNAs into appropriate vectors and transforming the vectors into host cells. In this case, the cloning vector, PSPORT, previously used for the generation of the cDNA library, is used to express IMP-2 in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein or fragments thereof. Sequences encoding IMP-2 fusion proteins lacking the hydrophobic stretches located at residues 53–76 of SEQ ID NO:1 (this stretch may anchor IMP-2 in the membrane) are preferentially employed for the production of soluble forms of recombinant IMP-2. The signal residues present on the PSPORT vector direct the secretion of IMP-2 into the bacterial growth media which can be used directly in the following assay for activity.

Alternatively, IMP-2 may be expressed as a membrane-bound protein in a host cell and the recombinant IMP-2 recovered from the membrane of the host cell using techniques well known to the art.

IX Demonstration of IMP-2 Activity

Given the chemical and structural similarity between the human IMP-2 and mouse E25AMM proteins, IMP-2 is presumed to be a type II integral membrane protein. To demonstrate that IMP-2 is an integral membrane protein, sequences encoding IMP-2 are expressed in cells which lack the ability to express IMP-2 and the location of IMP-2 is ascertained using conventional techniques (e.g., immuno-precipitation of proteins derived from cell membrane-containing fractions and soluble fractions lacking membrane associated proteins; preparation of anti-IMP-2 antibodies is described below). Expression of IMP-2 is achieved using methods known to the art as described above; numerous expression vectors are available for the expression of proteins in eukaryotic and prokaryotic hosts. Cells which lack the ability to express human IMP-2 are easily obtained as any non-human eukaryotic cell line is expected to lack the ability to express human IMP-2; in addition, prokaryotic cells would lack the ability to express IMP-2. Confirmation that a cell lacks the ability to express IMP-2 is obtained by a variety of means known to the art including Northern blot analysis in which RNA isolated from the candidate host cell is hybridized with IMP-2-encoding sequences (e.g., SEQ ID NO:2); cells whose RNA fails to hybridize with IMP-2 sequences are suitable IMP-2-negative host cells. In addition, anti-IMP-2 antibodies can be used to confirm that the candidate host cell lacks proteins which react or cross-react with IMP-2.

As described above, a reduction in IMP-2 expression is seen in diseased liver tissues. This suggests that increasing the expression of IMP-2 in liver disease may have a therapeutic effect. Expression vectors capable of directing the expression of IMP-2 in liver tissue (e.g., using a liver-specific promoter such as the albumin promoter) are used to increase the expression of IMP-2 in the liver of an animal suffering from liver disease. A portion of the diseased liver is removed (explanted) and the expression vector is transferred into the explanted liver cells ex vivo and the cells containing the IMP-2 expression vector are returned to the animal. Alternatively, IMP-2 encoding sequences under the control of a liver-specific promoter may be transferred directly to the liver of an animal using a suitable vector (e.g., retroviral vectors, adenoviral vectors, direct injection of DNA, etc.) using techniques known to the art. Liver function is monitored in animals receiving the IMP-2 sequences and in control animals which do not receive IMP-2 sequences (both diseased and disease-free or normal animals are employed as controls); liver function may be assessed by measurement of the serum level of aminotransferases, bilirubin, albumin y-globulin and measurement of the pro-thrombin time. An improvement in liver function in diseased animals which received IMP-2 sequences indicates the therapeutic effect of increasing IMP-2 expression in liver disease.

X Production of IMP-2 Specific Antibodies

IMP-2 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring IMP-2 Using Specific Antibodies

Naturally occurring or recombinant IMP-2 is substantially purified by immunoaffinity chromatography using antibodies specific for IMP-2. An immunoaffinity column is constructed by covalently coupling IMP-2 antibody to an activated chromatographic resin, such as CnBr-activated Sepharose (Pharmacia & Upjohn). After the coupling, the resin is blocked and washed according to the manufacturer's instructions.

Media containing IMP-2 is passed over the immunoaffinity column, and the column is washed under conditions that allow the preferential absorbance of IMP-2 (e.g., high ionic strength buffers in the presence of detergent). The column is eluted under conditions that disrupt antibody/IMP-2 binding (eg, a buffer of pH 2–3 or a high concentration of a chaotrope, such as urea or thiocyanate ion), and IMP-2 is collected.

XII Identification of Molecules Which Interact with IMP-2

IMP-2 or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled IMP-2, washed and any wells with labeled IMP-2 complex are assayed. Data obtained using different concentrations of IMP-2 are used to calculate values for the number, affinity, and association of IMP-2 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. A composition comprising the polynucleotide sequence of claim 1.

3. An isolated and purified polynucleotide sequence comprising SEQ ID NO:2.

4. An isolated and purified polynucleotide sequence which is fully complementary to SEQ ID NO:2.

5. A composition comprising the polynucleotide sequence of claim 4.

6. An expression vector containing the polynucleotide sequence of claim 1.

7. A host cell containing the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide from the host cell culture.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 266 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: NEUTGMT01
        ( B ) CLONE: 632664

( x i ) SEQUENCE DESCRIPTION: SEQ ID NO:1:

```
Met Val Lys Val Thr Phe Asn Ser Ala Leu Ala Gln Lys Glu Ala Lys
 1               5                  10                  15

Lys Asp Glu Pro Lys Ser Gly Glu Glu Ala Leu Ile Ile Pro Pro Asp
            20                  25                  30

Ala Val Ala Val Asp Cys Lys Asp Pro Asp Asp Val Val Pro Val Gly
        35                  40                  45

Gln Arg Arg Ala Trp Cys Trp Cys Met Cys Phe Gly Leu Ala Phe Met
    50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys Gly Ile Lys Tyr Ile Lys Asp
                85                  90                  95

Asp Val Ile Leu Asn Glu Pro Ser Ala Asp Ala Pro Ala Ala Leu Tyr
            100                 105                 110

Gln Thr Ile Glu Glu Asn Ile Lys Ile Phe Glu Glu Glu Glu Val Glu
        115                 120                 125
```

```
Phe  Ile  Ser  Val  Pro  Val  Pro  Glu  Phe  Ala  Asp  Ser  Asp  Pro  Ala  Asn
     130                 135                      140

Ile  Val  His  Asp  Phe  Asn  Lys  Lys  Leu  Thr  Ala  Tyr  Leu  Asp  Leu  Asn
145                      150                      155                           160

Leu  Asp  Lys  Cys  Tyr  Val  Ile  Pro  Leu  Asn  Thr  Ser  Ile  Val  Met  Pro
                    165                 170                           175

Pro  Arg  Asn  Leu  Leu  Glu  Leu  Leu  Ile  Asn  Ile  Lys  Ala  Gly  Thr  Tyr
                    180                      185                      190

Leu  Pro  Gln  Ser  Tyr  Leu  Ile  His  Glu  His  Met  Val  Ile  Thr  Asp  Arg
               195                      200                      205

Ile  Glu  Asn  Ile  Asp  His  Leu  Gly  Phe  Phe  Ile  Tyr  Arg  Leu  Cys  His
     210                      215                      220

Asp  Lys  Glu  Thr  Tyr  Lys  Leu  Gln  Arg  Arg  Glu  Thr  Ile  Lys  Gly  Ile
225                      230                      235                           240

Gln  Lys  Arg  Glu  Ala  Ser  Asn  Cys  Phe  Ala  Ile  Arg  His  Phe  Glu  Asn
                    245                      250                      255

Lys  Phe  Ala  Val  Glu  Thr  Leu  Ile  Cys  Ser
                    260                 265
```

( 2 ) INFORMATION FOR SEQ ID NO:2:

( i ) SEQUENCE CHARACTERISTICS:
        ( A ) LENGTH: 1114 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: NEUTGMT01
        ( B ) CLONE: 632664

( x i ) SEQUENCE DESCRIPTION: SEQ ID NO:2:

```
GCCGCCTCTG  CCGCCGCGGA  CTTCCCGAAC  CTCTTCAGCC  GCCCGGAGCC  GCTCCCGGAG    60
CCCGGCCGTA  GAGGCTGCAA  TCGCAGCCGG  TGAGCCCGCA  GCCCGCGCCC  CGAGCCCGCC   120
GCCGCCCTTC  GAGGGCGCCC  CAGGCCGCGC  CATGGTGAAG  GTGACGTTCA  ACTCCGCTCT   180
GGCCCAGAAG  GAGGCCAAGA  AGGACGAGCC  CAAGAGCGGC  GAGGAGGCGC  TCATCATCCC   240
CCCCGACGCC  GTCGCGGTGG  ACTGCAAGGA  CCCAGATGAT  GTGGTACCAG  TTGGCCAAAG   300
AAGAGCCTGG  TGTTGGTGCA  TGTGCTTTGG  ACTAGCATTT  ATGCTTGCAG  GTGTTATTCT   360
AGGAGGAGCA  TACTTGTACA  AATATTTGC   ACTTCAACCA  GATGACGTGT  ACTACTGTGG   420
AATAAAGTAC  ATCAAAGATG  ATGTCATCTT  AAATGAGCCC  TCTGCAGATG  CCCCAGCTGC   480
TCTCTACCAG  ACAATTGAAG  AAAATATTAA  AATCTTTGAA  GAAGAAGAAG  TTGAATTTAT   540
CAGTGTGCCT  GTCCCAGAGT  TTGCAGATAG  TGATCCTGCC  AACATTGTTC  ATGACTTTAA   600
CAAGAAACTT  ACAGCCTATT  TAGATCTTAA  CCTGGATAAG  TGCTATGTGA  TCCCTCTGAA   660
CACTTCCATT  GTTATGCCAC  CCAGAAACCT  ACTGGAGTTA  CTTATTAACA  TCAAGGCTGG   720
AACCTATTTG  CCTCAGTCCT  ATCTGATTCA  TGAGCACATG  GTTATTACTG  ATCGCATTGA   780
AAACATTGAT  CACCTGGGTT  TCTTTATTTA  TCGACTGTGT  CATGACAAGG  AAACTTACAA   840
ACTGCAACGC  AGAGAAACTA  TTAAAGGTAT  TCAGAAACGT  GAAGCCAGCA  ATTGTTTCGC   900
AATTCGGCAT  TTTGAAAACA  AATTTGCCGT  GGAAACTTTA  ATTTGTTCTT  GAACAGTCAA   960
GAAAAACATT  ATTGAGGAAA  ATTAATATCA  CAGCATAACC  CCACCCTTTA  CATTTTGTGC  1020
AGTGATTATT  TTTTAAAGTC  TTCTTTCATG  TAAGTAGCAA  ACAGGGCTTT  ACTATCTTTT  1080
CATCTCATTA  ATTCAATTAA  AACCATTACC  TTAA                                1114
```

( 2 ) INFORMATION FOR SEQ ID NO:3:

( i ) SEQUENCE CHARACTERISTICS:
        ( A ) LENGTH: 263 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 624778

( x i ) SEQUENCE DESCRIPTION: SEQ ID NO:3:

```
Met Val Lys Ile Ala Phe Asn Thr Pro Thr Ala Val Gln Lys Glu Glu
 1               5                  10                 15
Ala Arg Gln Asp Ile Glu Ala Leu Val Ser Arg Thr Val Arg Ala Gln
                20                 25                 30
Ile Leu Thr Gly Lys Glu Leu Arg Val Val Pro Gln Glu Lys Asp Gly
            35                 40                 45
Ser Ser Gly Arg Cys Met Leu Thr Leu Leu Gly Leu Ser Phe Ile Leu
        50                 55                 60
Ala Gly Leu Ile Val Gly Gly Ala Cys Ile Tyr Lys Tyr Phe Met Pro
65                      70                 75                 80
Lys Ser Thr Ile Tyr His Gly Glu Met Cys Phe Phe Asp Ser Glu Asp
                85                 90                 95
Pro Val Asn Ser Ile Pro Gly Gly Glu Pro Tyr Phe Leu Pro Val Thr
            100                105                110
Glu Glu Ala Asp Ile Arg Glu Asp Asp Asn Ile Ala Ile Ile Asp Val
        115                120                125
Pro Val Pro Ser Phe Ser Asp Ser Asp Pro Ala Ala Ile Ile His Asp
    130                135                140
Phe Glu Lys Gly Met Thr Ala Tyr Leu Asp Leu Leu Gly Asn Cys
145                 150                155                160
Tyr Leu Met Pro Leu Asn Thr Ser Ile Val Met Thr Pro Lys Asn Leu
                165                170                175
Val Glu Leu Phe Gly Lys Leu Ala Ser Gly Lys Tyr Leu Pro His Thr
            180                185                190
Tyr Val Val Arg Glu Asp Leu Val Ala Val Glu Glu Ile Arg Asp Val
        195                200                205
Ser Asn Leu Gly Ile Phe Ile Tyr Gln Leu Cys Asn Asn Arg Lys Ser
    210                215                220
Phe Arg Leu Arg Arg Arg Asp Leu Leu Leu Gly Phe Asn Lys Arg Ala
225                 230                235                240
Ile Asp Lys Cys Trp Lys Ile Arg His Phe Pro Asn Glu Phe Ile Val
                245                250                255
Glu Thr Lys Ile Cys Gln Glu
                260
```

( 2 ) INFORMATION FOR SEQ ID NO:4:

( i ) SEQUENCE CHARACTERISTICS:
        ( A ) LENGTH: 1635 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 624777

(xi) SEQUENCE DESCRIPTION: SEQ ID NO:4:

```
GGGAGACCTG AGCTCGCTGC TGCCTGTGGA AGACTGGGAG AGGAGACACT AAGTGCTGCT    60
CAAGCAAGCG CGATCCTCTC CTCTTTCAAC CTGCAGCCCA AGATACTGAT TCGAGCCGCG   120
CCTTACCGCG CAGCCCGAAG ATTCACCATG GTGAAGATCG CCTTCAACAC CCCTACGGCG   180
GTGCAAAAGG AGGAGGCGCG GCAAGATATA GAGGCGCTCG TCAGTCGCAC TGTCCGAGCT   240
CAAATCCTGA CTGGCAAGGA GCTCAGAGTT GTCCCGCAGG AGAAAGATGG CTCATCTGGG   300
AGATGCATGC TTACTCTCCT AGGCCTCTCA TTCATCTTGG CAGGACTGAT TGTTGGTGGA   360
GCCTGCATTT ACAAGTACTT CATGCCCAAG AGCACCATTT ACCATGGTGA GATGTGCTTC   420
TTTGATTCTG AGGATCCTGT CAATTCCATT CCTGGAGGAG AGCCATACTT TCTGCCTGTG   480
ACTGAGGAGG CTGATATCCG TGAGGATGAC AACATTGCCA TCATTGATGT GCCTGTGCCC   540
AGTTTCTCTG ATAGCGATCC GGCGGCAATT ATTCACGACT TTGAGAAGGG AATGACTGCT   600
TACCTGGACT TGCTTTTGGG AAACTGTTAT CTGATGCCCC TCAATACTTC CATTGTTATG   660
ACTCCAAAGA ATCTGGTGGA ACTTTTTGGA AAACTGGCAA GTGGCAAGTA TTTGCCTCAT   720
ACTTATGTGG TTCGTGAAGA CCTGGTTGCT GTGGAAGAAA TTCGTGATGT TAGTAACCTT   780
GGTATTTTTA TTTACCAACT TTGCAACAAC CGAAAATCCT TCCGCCTTAG ACGCAGAGAC   840
CTTCTGCTGG GTTTCAACAA GCGTGCCATT GACAAATGCT GGAAGATTAG ACACTTCCCC   900
AATGAATTTA TCGTTGAAAC CAAGATCTGT CAGGAGTGAA ATGTGACAGA TAAAGAGTAT   960
CCTTGATAAT AAGAAGTCAG GAACTTACCG TCTGACTTGG AAAATTGAAA TTGATGGGAT  1020
ACTCATGCTA TTTACTCATA CATTTACTCT ATTGCTTATA CTGGAAAAGG AAAGGGAAAG  1080
GGGGGAGAAA ACTACTAACC ACTGCAAGCG ATTGTCCAAT TCTACTTTAA TTGACATTGC  1140
TTGCTGTTTT CAACAAGTCA AATGATTATC TTTTCTCTTG AATTTATAGG GTTTAGATTT  1200
CTGAAAGCAG CATGAATGTG TCATCTTACC ATCCTGACAA TAAAGCCCAT CCTCTGGTTT  1260
TATTTAAAGC AAGCTCTTTC CAACATCACT TGGCTAGAGC ATGCTTTAAA TTTAAAATAT  1320
TTGAAATTTG TTTTTGACAT TTTTTTGTGT GAAACATGTC AAATCTCTTA CCATTCTTTG  1380
GTTTTCTTCT TTATTATGTT CAACTCTCCT GATTTCAGAA GTTACATTTT TGCATTTCTA  1440
TCAGGTGCTG TGTAACGAAT CTGACTGATA TGTGAACAAT CTTCATGAGG AAGCAATTTT  1500
TTACTCATGT AATGATTCTT TCTCACTGAT ATCTGTATTG TGAAATCCAC AGAACTGTAC  1560
AGGTGCTGAA TGCTGTAAGG AGTTCTGGTT GTATGAATTC TACAACCCTA TAATAAAGTT  1620
TACCGTATTC AATCA                                                  1635
```